United States Patent [19]

Castino et al.

[11] Patent Number: 5,456,835
[45] Date of Patent: Oct. 10, 1995

[54] DEVICE AND PROCESS FOR REMOVING FREE HEMOGLOBIN FROM BLOOD

[75] Inventors: Franco Castino, Sudbury; Abdul R. M. Azad, Northborough; Eric K. Lee, Acton, all of Mass.

[73] Assignee: Hemasure, Inc., Marlborough, Mass.

[21] Appl. No.: 148,883

[22] Filed: Nov. 8, 1993

[51] Int. Cl.$^6$ .......................... B01D 37/00; B01D 39/04; B01D 39/08; B01D 15/00

[52] U.S. Cl. .......................... 210/645; 210/490; 210/505; 210/508; 210/767; 435/2; 435/179; 435/181; 436/177; 436/53; 530/385; 530/412; 530/814; 530/816

[58] Field of Search .................................. 210/490, 491, 210/505, 508, 645, 767; 428/283, 286, 287, 323, 327; 435/2, 179, 181; 436/177, 530, 15; 530/385, 412, 413, 814, 816

[56] References Cited

U.S. PATENT DOCUMENTS

| | | | |
|---|---|---|---|
| 4,274,914 | 6/1981 | Keith et al. | 162/109 |
| 4,925,574 | 5/1990 | Hsia | 210/635 |
| 5,059,654 | 10/1991 | Hou et al. | 210/502.1 |
| 5,190,657 | 3/1993 | Heagle et al. | 210/645 |

FOREIGN PATENT DOCUMENTS

| | | |
|---|---|---|
| 0468585A2 | 1/1992 | European Pat. Off. . |
| 9005018 | 5/1990 | WIPO . |

OTHER PUBLICATIONS

Hermanson et al. "Immobilized Affinity Ligand Techniques" *Smith Academic Press, Inc.* 51–132 (1992).

Dean et al. "Affinity Chromatography A practical Approach" *IRL Press Ltd.* 31–59 (1987).

Axen et al., "Chemical Coupling of Peptides and Proteins to Polysacchardies by Means of Cyanogen Halides" *Nature* 214, 1302–1304 (1967).

Cuatrecasas et al. "Selective Enzyme Purification by Affinity Chromatography" *Proc. Natl. Acad. Sci. US* 61, 636–643 (1968).

Lamed et al., "Covalent Coupling of Nucleotides to Agarose For Affinity Chromatography", *Biochimica et Biophysica Acta*, 304. 231–235 (1973).

Hou et al., "A Method for Extracorporeal Heparin Removal from Blood by Affinity Chromatography", *Artif Organs*, 14(6), 436–442 (1990).

*Primary Examiner*—John Kim
*Attorney, Agent, or Firm*—Heslin & Rothenberg

[57] ABSTRACT

A filter and a hollow-fiber or flat-sheet membrane for removing hemoglobin from whole blood or blood fractions are disclosed. The filter comprises a laid textile web which has been modified to attach a ligand for hemoglobin. The membrane comprises a polyethersulfone membrane that has been similarly modified. Methods for removing hemoglobin, cellular components and debris from blood are also disclosed.

8 Claims, 1 Drawing Sheet

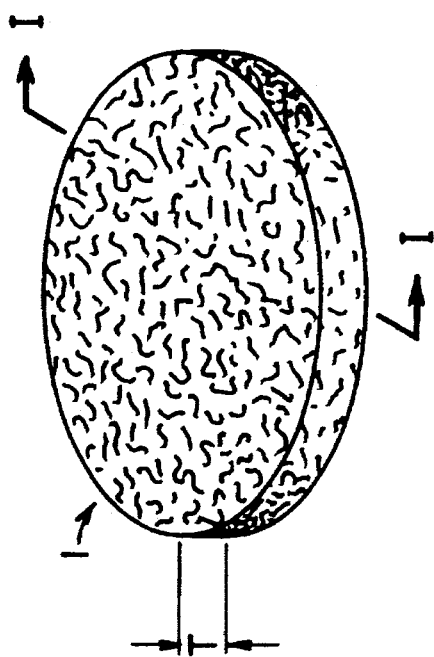
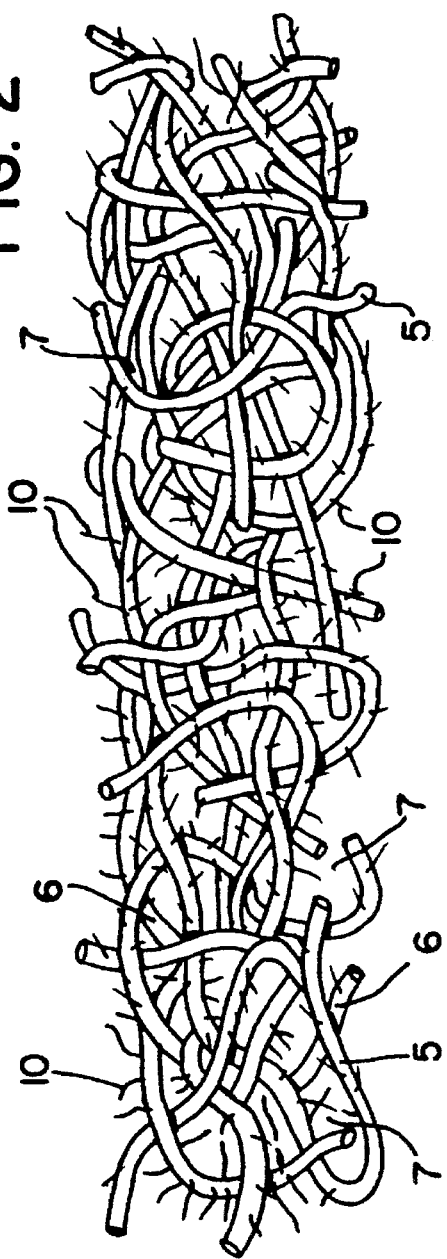

DEVICE AND PROCESS FOR REMOVING FREE HEMOGLOBIN FROM BLOOD

CROSS-REFERENCE TO RELATED APPLICATIONS

Certain embodiments of the present invention employ modifications of membranes described in application Ser. No. 07/956432, now abandoned, the entire disclosure of which is incorporated herein by reference.

FIELD OF THE INVENTION

The invention relates to filters or hollow fiber membranes for removing free hemoglobin from whole blood or blood fractions, methods for preparing said filters and membranes and methods for using the membranes and filters to remove hemoglobin from whole blood or blood fractions.

BACKGROUND OF THE INVENTION

Blood products, especially those intended for transfusion, are non-homogeneous in that they include several cell types as well as a variety of molecular components having differing biological activities. Often patients into whom the blood is to be transfused are only in need of one component (e.g. red blood cells for gas transport), and the other components present in the blood product are not only unnecessary but may even be disadvantageous or harmful.

In particular, in the field of autologous transfusion, when the patient's own blood is recovered before, during or after surgery and is purified before being returned to the same individual, the recovery of autologous blood presents a technical challenge. Autologous transfusion is beneficial from a medical standpoint because many of the epidemiological and immunological problems associated with the use of donor blood are avoided. However, in such procedures as open heart surgery, a significant volume of the patient's blood (1 to 3 liters) is in the extracorporeal circuit associated with heart-lung machines. This blood is diluted with crystalloid solutions used to prime the machine, is heavily anticoagulated with heparin to prevent clot formation, and contains free hemoglobin and potassium derived from red blood cells damaged during the surgical procedure. To use this blood for autologous transfusion, the unwanted constituents (water, heparin, free hemoglobin and potassium) must be removed. In other intra-operative blood recovery procedures, such as in thoracic and orthopedic surgery, the patient's blood is typically suctioned from the open wound and subjected to cleansing procedures. The blood salvaged in this manner is considerably more contaminated than that recovered from heart-lung machines, since it contains fragments of tissues generated by surgery, in addition to the contaminants mentioned above.

Currently, two techniques are used to remove contaminants: the first relies upon washing fluids and associated equipment such as centrifuges. In addition to the mechanical complexity of a system that involves centrifuging, this technique requires the addition of buffer solutions that must then be removed, and it provides red blood cell (RBC) fractions depleted of all plasma proteins. The second, which is based on depth dead-end filtration, may be broadly divided into two classes: blood sieves and blood component filters. Blood sieves are very coarse in pore size and have a strong tendency to block quickly if the pore size is finer than a minimum. They are used primarily for removing large particles such as bone chips, tissue fragments, agglomerates and the like from blood. Blood component filters are used primarily for removing selected natural blood components such as leukocytes. They are incapable of removing small molecules such as hemoglobin.

In addition to surgical transfusion with autologous blood, a second major utility for a blood filter that could remove small molecules is found in the reconstitution of stored blood. One of the methods commonly used for the preservation of packed red blood cells is storage of the frozen cells at −80° C. The process involves the addition of cryoprotectant agents (commonly glycerine), freezing the cells, thawing, and finally washing the cells to remove the cryoprotectant. The freezing and thawing cause lysis of the red cells and the release of free hemoglobin.

Free hemoglobin in whole blood and blood fractions is undesirable due to its toxicity, a particularly severe complication being renal toxicity. Thus, it would be advantageous to have a device and method to remove free hemoglobin from whole blood and blood fractions.

It is known that hemoglobin can be obtained from solution by affinity chromatography. For example, U.S. Pat. No. 4,925,574 to Hsia describes an agarose gel to which are attached various hemoglobin ligands for affinity chromatography. This appears to be a useful technique when obtaining hemoglobin is the object, but it cannot be used to remove hemoglobin from whole blood or blood fractions when obtaining the blood is the object because (a) gels are mechanically unstable, (b) gels are impenetrable to cellular components and (c) many gel substrates induce lysis and release of hemoglobin (see below).

It would therefore be highly desirable to have a method for removing hemoglobin along with other debris from whole blood or blood fractions quickly and efficiently.

SUMMARY OF THE INVENTION

It is an object of the present invention to provide a filter for removing hemoglobin from whole blood or blood fractions quickly, safely and without inducing hemolysis.

It is a further object to provide a filter for removing leukocytes, hemoglobin and debris from blood or blood fractions.

It is a further object to provide a method for attaching hemoglobin ligands to commercially available filters.

It is a further object to provide a method of removing free hemoglobin from whole blood or blood fractions. It is an advantage of the invention that the foregoing objects can be accomplished quickly, safely and inexpensively. It is a further advantage that only about 25% of plasma proteins are lost from the RBC fraction.

These and other objects, features and advantages are realized by the present invention which, in one aspect relates to a filter for removing hemoglobin from whole blood or a blood fraction comprising a shape-sustaining laid textile web having a thickness of 1 to 8 mm and a bulk density of 0.05 to 0.4 g/cm³, said web comprising:

(a) a plurality of interlocked textile fibers with average deniers between 0.05 and 0.75 and average lengths between 3 mm and 15 mm, said textile fibers being substantially uniformly distributed in said web so as to form a matrix of the textile fibers with spaces between adjacent interstices of interlocked fibers; and (b) a plurality of fibrillated particles of surface-modified polymeric material having a surface area of 5 to 60 square meters per gram substantially disposed within said spaces of the matrix, said fibrillated particles having a plurality of fine fibrils which are interlocked with adjacent textile fibers of said spaces such that the fibrillated particles are not substantially displaceable from said web during filtration of said blood;

wherein the weight ratio of the fibrillated particles to the textile fibers is between 1:99 and 40:60; and wherein said surface-modified polymeric material is a hemolytically inert polymer covalently linked to a ligand for hemoglobin; and wherein said textile fibers are hemolytically inert and stable to alkaline hydrolysis.

In a preferred embodiment the surface modified polymeric material is a cellulose ester, most preferably cellulose acetate. The ligand for hemoglobin may be inositol hexaphosphate, adenosine triphosphate (ATP), pyridoxal phosphate, 2,3-diphosphoglycerate (DPG), adenosine diphosphate or adenosine phosphate. Preferably, the ligand is ATP or DPG. The ligand may be attached to the cellulose ester through a dihydrazide or diamine linker, preferably adipic dihydrazide. The textile fibers in the filter may be one or more of polyolefin, polyamide, polysulfone, polyester, polyvinyl alcohol and poly(ethylene-vinyl alcohol) copolymer fibers; polyolefin or polyolefin-sheathed fibers are preferred.

In another aspect the invention relates to a method for producing a hemoglobin filter comprising:
(a) providing a shape-sustaining web comprising:
  (1) a plurality of fibers that are resistant to alkaline degradation; and
  (2) a plurality of cellulose acetate fibers;
(b) treating said web with aqueous base to hydrolyze a portion of cellulose acetate esters to the corresponding free hydroxyls;
(c) activating said free hydroxyls to produce amine-reactive residues;
(d) reacting said amine-reactive residues with a diamine or a dihydrazide; and
(e) reacting the resulting amine or hydrazide with an activated derivative of adenosine triphosphate (ATP) or 2,3-diphosphoglycerate (DPG).

A particular embodiment of the general method produces a hemoglobin filter by:
(a) providing a shape-sustaining laid textile web having a thickness of 1 to 8 mm and a bulk density of 0.05 to 0.4 g/cm$^3$, said web comprising:
  (1) a plurality of interlocked polyolefin or mixed polyolefin sheathed and polyethylene terphthalate (PET) fibers with average deniers between 0.05 and 0.75 and average lengths between 3 mm and 15 mm, said fibers being substantially uniformly distributed in said web so as to form a matrix of the fibers with spaces between adjacent interstices of interlocked fibers; and
  (2) a plurality of fibrillated cellulose acetate particles having a surface area of 5 to 60 square meters per gram substantially disposed within said spaces of the matrix, said fibrillated particles having a plurality of fine fibrils which are interlocked with adjacent polyolefin or PET/polyolefin fibers of said spaces such that the fibrillated particles are not substantially displaceable from said web during filtration of blood, wherein the weight ratio of the fibrillated particles to the polyolefin or PET/polyolefin fibers is between 1:99 and 40:60; and
(b) treating said web with aqueous base to hydrolyze a portion of cellulose acetate esters to cellulose containing corresponding free hydroxyls;
(c) activating said free hydroxyls to produce amine-reactive residues;
(d) reacting said amine-reactive residues with a diamine or a dihydrazide; and
(e) reacting the resulting amine or hydrazide with an activated derivative of adenosine triphosphate (ATP) or 2,3-diphosphoglycerate (DPG).

In one embodiment the web is treated with 1N aqueous sodium or potassium hydroxide at 20° to 40° for 8 to 312 hours. Variations of the parameters such as the concentration of the sodium hydroxide solution, the nature of the base (e.g. potassium hydroxide) the temperature and time can be used to provide the necessary modification of the polymeric material.

Methods of activating the free hydroxyls, either directly or indirectly, include reaction with periodates, cyanogen bromide, carbonyl diimidazole, divinyl sulfone, azlactones, sulfonyl chlorides, diepoxides, dihalides, halo-epoxides, 2,4,6-trichloro-S-triazine, 2-fluoro-1-methylpyridinium salts, disulfonyl chlorides, diacid chlorides, triacid chlorides, 2-ethoxy-1-ethoxycarbonyl-1,2-dihydroquinoline, diisocyanates, haloacetic acid followed by N-hydroxysuccinimide and a carbodiimide and other similar processes. Preferred methods of activating the free hydroxyls include reaction with cyanogen bromide and reaction with periodates. The amine reactive residues are preferably reacted with adipic dihydrazide to produce a plurality of N-monosubstituted hydrazides or with ethylenediamine to produce N-monosubstituted diamines, which are reacted with periodate-oxidized ATP or carbodiimide-activated DPG.

In a further aspect the invention relates to a method for removing hemoglobin from whole blood or a blood fraction comprising passing the blood through a filter as described above.

In another aspect the invention relates to a hollow-fiber or flat-sheet membrane for removing hemoglobin from a blood fraction or whole blood comprising:
(a) polyethersulfone (PES) as the primary hydrophobic polymer component, said PES having functionalizable phenolic chain ends;
(b) a first linker moiety attached to a plurality of said phenolic chain ends, said first linker derived from an oxirane selected from the group consisting of ethylene glycol diglycidyl ether, 1,4-butanediol diglycidyl ether and epichlorohydrin; and
(c) a surface-modified polymeric material attached to a plurality of said first linker moieties, said surface-modified polymeric material consisting of a hemolytically inert polymer covalently attached to a plurality of ligands for hemoglobin.

In one embodiment the surface modified polymeric material is a hydroxyalkylcellulose covalently attached through a second linker moiety to a plurality of ligands for hemoglobin. In a second embodiment the surface modified polymeric material is a polyethyleneimine covalently attached through a second linker moiety to a plurality of ligands for hemoglobin. Exemplary and preferred ligands are as before. In a preferred embodiment the ligand is attached to polyethyleneimine via a dihydrazide second linker moiety, or hydroxyalkylcellulose via a dihydrazide or diamine second linker moiety, preferably adipic dihydrazide or ethylenediamine.

In a further aspect the invention relates to a method for removing hemoglobin from whole blood or a blood fraction comprising providing flowing contact between the blood and a flat-sheet or hollow-fiber membrane as described above.

BRIEF DESCRIPTION OF THE DRAWINGS

FIG. 1 is a perspective view of a filter according to the invention in a configuration useful for placing in a filter carrier.

FIG. 2 is a diagrammatic partial cross-sectional view of a portion of the filter of FIG. 1, taken along line I—I.

DETAILED DESCRIPTION INCLUSIVE OR PREFERRED EMBODIMENTS

The present invention provides, in one embodiment, a filter for simultaneously removing free hemoglobin, leukocytes, and any other debris or components larger than about 8 μm in cross-section, and, in another embodiment, a hollow-fiber or flat-sheet membrane for removing primarily free hemoglobin, although it could be used for mechanical filtration based on particle size as well, if the membrane and apparatus were appropriately designed. The membrane could also, by proper modification, be used to remove both hemoglobin and a portion of the aqueous solution in which the free hemoglobin is found. As will be apparent, the filters and membranes could also be used to recover hemoglobin by displacing the bound hemoglobin from the filter or membrane with phosphate buffered saline (PBS) or other phosphate-containing eluent.

The filter is a modification of the filter described in U.S. Pat. No. 5,190,657, the disclosure of which is incorporated herein by reference. The figures from that patent are used in the following description for the sake of clarity. Briefly, the filter consists of a filter material which is a shape-sustaining laid textile web. As shown in FIG. 1, the web has been cut in a circular configuration to form the filter and is suitable for loading into a cylindrical filter carrier.

The thickness of the web is at least 1 millimeter, most preferably at least 2 millimeters, and can be up to about 8 mm. The density of the laid web is between about 0.05 and 0.4 g/cm$^3$.

As seen in FIG. 2, which is a highly diagrammatic illustration of a portion of a section of the filter of FIG. 1, the filter material is comprised of a plurality of matrix textile fibers 5, and these textile fibers have average deniers between about 0.05 and 0.75. At least 60%, preferably at least 70% and more preferably at least 80 to 85% of the fibers have deniers within the above-noted ranges, and lengths from 12,000 to 180,000 m/g.

As can be seen in FIG. 2, the textile fibers are substantially uniformly distributed through the web so as to form a matrix of the textile fibers. The matrix has spaces 7 between adjacent interstices 6 of the interlocked fibers. Within these spaces, there are a plurality of fibrillated particles 10 of very high surface area. The fibrillated particles 10 are disposed within spaces 7, as well as along and among the matrix textile fibers 5.

A portion of the matrix textile fibers 5 may have a sheath and a core with the deniers and lengths thereof being the same as described above. The sheath is of a low melt temperature polymer, and the core of a higher melt temperature polymer. When at least a portion of the matrix textile fibers of the filter material are the sheath/core fibers, the web of the filter material will have been subjected to temperatures such as to soften the polymer sheath and cause some bonding of the textile fibers together. Generally, from 5 to 35% of the matrix textile fibers are the sheath/core.

The matrix textile fibers are commonly synthetic polymer fibers, such as polyolefin or polyolefin-sheathed fibers, polyamide, polysulfone, polyester, polyvinyl alcohol and poly(ethylene-vinyl alcohol) copolymer fibers. Polyolefin fibers are quite resistant to alkaline hydrolysis and are therefore much to be preferred. A critical feature of both the textile fibers and the fibrils is that they be compatible with blood, and, in particular, that they not cause significant hemolysis. In a clinical situation, hemolysis that gives rise to more than 10% increase in free hemoglobin would be considered significant.

The sheath fiber, if used, has a core of the aforementioned textile fiber materials, a sheath of any low melting polymer. Polyolefin polymers, such as polyethylene or polypropylene, are preferred, since they provide sheaths with relatively low melting points, and it is easy to soften the sheaths to provide the required adherence. In addition, they are resistant to alkaline hydrolysis. The sheath will commonly be 5–30% of the core diameter.

The fibrillated particles are polyester fiber material, acrylic fiber material, nylon fiber material, polyolefin fiber material or cellulosic fiber material. Cellulose acetate is usually used since a great number of fibrils are produced with that material, and the material has a natural hydrophilic nature.

The filters used in the examples that follow are commercially available from Lydall Inc. (Manchester, Conn.) and consist of polypropylene fibers and cellulose acetate "fibrets." In general, any filter comprised of a cellulose acetate component and a shape-sustaining web that is resistant to base hydrolysis will function in the method of the invention.

Lydall polypropylene/cellulose acetate filter pads (1.9 mm thick, style 825B) are modified by immersing 90 mm diameter discs in aqueous alkaline solutions for varying lengths of time. The pads are washed extensively with water on a filter until the washings are close to neutral, and then dried in air at 30° to 40° C. This hydrolysis converts the cellulose acetate to cellulose containing free hydroxyl groups. Insufficient hydrolysis results in a very low number of hydroxyl groups available for subsequent reaction and hence a low capacity for hemoglobin in the resulting filter, whereas extensive hydrolysis results in the degradation of the cellulose substrate. In one embodiment the web is hydrolyzed with aqueous sodium hydroxide. Those skilled in the art will recognize that various temperatures, concentrations of sodium hydroxide and treatment times will affect the extent of hydrolysis and the degradation of the substrate. Generally, treatment conditions comprising sodium hydroxide concentrations higher than 0.1N but lower than 5N at temperatures lower than 60° C., and treatment times of about 8 hours to 13 days provide adequate hydrolysis without excessive degradation of the substrate, as indicated by the efficiency of leukocyte removal and red blood cell (RBC) passage. For these particular pads, it has been found that treatment with 1N sodium hydroxide at room temperature for more than 8 hours and up to 312 hours provides adequate hydrolysis and acceptable degradation of the substrate. It is expected that other bases, such as potassium hydroxide, lithium hydroxide, etc. would function similarly.

The "hydrolyzed pads" i.e. having free cellulose OH functionalities, can be activated by any of the commonly known methods. See *Immobilized Affinity Ligand Techniques*, Greg T. Hermanson, A. Krisna Mallia, and Paul K. Smith Academic Press, Inc., San Diego Calif., (1992), p. 51–132, and *Affinity Chromatography, A practical Approach*, Edited by P. D. G. Dean, W. S. Johnson and F. A. Middle, p. 31–59, IRL Press Ltd. Eynsham, Oxford OX81JJ, England (1987) and U.S. Pat. No. 3,389,142, the disclosures of which are incorporated herein by reference. Two preferred methods include cyanogen bromide activation and periodate activation.

Cyanogen bromide reacts with vicinal diols of cellulose to provide imidocarbonate and/or cyanate intermediates. These are highly activated toward nucleophilic attack and can be subsequently reacted with linkers or ligands containing primary amines. The result of the reaction is a ligand or linker covalently attached to the cellulose through a carbamate. The activation reaction is carried out as described by Axen et al. [*Nature* 214, 1302–1304 (1967)] and Cuatrecasas et al. [*Proc. Nat. Acad. Sci. US* 61, 636–643 (1968)] or minor modifications thereof.

Periodate activation involves the periodate-induced oxidative cleavage of vicinal diols to aldehydes, which are similarly reactive toward primary amines in the linker or ligand. A reduction step with sodium cyanoborohydride or similar reducing agent is commonly employed to convert the somewhat hydrolytically labile Schiff base to an alkylamine. These reactions are well known to persons of skill in the art.

In the case where a ligand contains primary amine groups that are not required for its interaction with hemoglobin, it can, in principle, be attached directly to the activated cellulose as described above. However, in most cases an amine-containing linker will be employed to provide a bridge between the cellulose and the ligand. There are several reasons for employing a linker: (1) the ligand may not have a useable primary amine group, (2) the chemistry to provide stable covalent bonds may be more readily carried out on the linker, and (3) it may be desirable to provide the ligand with some degree of mobility to allow it better access to the binding site on its target molecule (hemoglobin); in this respect the linker functions as a sort of tether between the ligand and the relatively rigid polymer (cellulose) backbone. In most of the examples that follow, adipic dihydrazide has been employed as the linker, but any difunctional amine (e.g. hexamethylenediamine) or dihydrazine could be used.

It is known that hemoglobin specifically binds small polyanionic molecules, especially 2,3-diphosphoglycerate (DPG) and adenosine triphosphate (ATP). These are therefore particularly attractive as ligands for attachment to the cellulose of the filter, although the invention is not restricted to DPG and ATP. Other ligands now known or subsequently discovered are expected to function similarly. In the case of ATP the ribose residue may be activated with cyanogen bromide or periodate as was the case with cellulose. A preferred method is the periodate oxidation described by Lamed et al. [*Biochim. Biophys. Acta* 304, 231–235 (1973)] which is incorporated herein by reference. The activated ligand is then reacted with the amine functionality of the linker as described above for reaction of activated cellulose with linker. In the case of DPG the carboxylic acid residue may be activated with a carbodiimide.

Among known ligands for human hemoglobin, ATP and DPG are preferred because of their reasonable binding constants and low toxicity. Other possible ligands include inositol hexaphosphate, pyridoxal phosphate, ADP and phosphate. Pyridoxal phosphate and inositol hexaphosphate are less attractive because their toxicity would pose a problem if they were to leach from the filter. ADP and adenosine monophosphate are less attractive because their lower affinity for human hemoglobin would be reflected in a lower efficiency of a filter that employed them as ligands.

The foregoing chemistry, which was applied to the creation of filters for the removal of hemoglobin, can also be applied to the creation of hollow-fiber or flat-sheet membranes for the removal of hemoglobin. In this case, hollow-fiber membranes are prepared according to the methods of copending application 07/956,432, particularly pages 75–77. The resulting hydrazide-derivatized hollow-fibers are then treated as above to attach the ligand.

The examples which follow include some experiments wherein the ligand for hemoglobin was attached to an amine-modified methacrylamide gel which was itself supported in a silica matrix (so-called Hyper D$^{TM}$ beads) to help surmount the generic liability of gels: lack of mechanical stability. These experiments do not represent prior art, but rather experiments directed toward defining the present invention. As will be seen from Table IV below, the results were unsatisfactory in that the amine-modified methacrylamide appears to have induced hemolysis, thereby increasing rather than decreasing the levels of free hemoglobin.

EXAMPLES

Preparation of Modified Matrices

A. Preparation of filters with ATP covalently attached

Polypropylene/cellulose acetate filter pads (1.9 mm thick, style 825B, Lydall Westex, P.O. Box 109, Hamptonville, N.C. 27020) were modified by immersing 90 mm diameter discs in 1N sodium hydroxide solutions for 44 hours at room temperature. The pads were washed extensively with water on a filter until the washings were close to neutral, and then dried in air at 30° C.

1. Cyanogen Bromide (CNBr) Activation

Unhydrolyzed pads and pads hydrolyzed for 8 hours in 1N sodium hydroxide were used as starting material. A standard procedure was used, keeping the ratio of 2 g of CNBr per gram of filter pads (4 g CNBr/90 mm diameter disc). The filter pads were placed in 500 mL Nalgene plastic filter holders, the bottom, porous membranes of which had been removed to improve flow rate. The filter pads were treated with the CNBr by repeated filtration. The CNBr activated pads were then reacted with a saturated solution of adipic dihydrazide (approximately 90 g/L) in 0.1M sodium carbonate buffer (pH 9.5), and the reaction was allowed to proceed overnight at 4° C., as described by Lamed et al. for agarose beads. The hydrazide-treated pads may be further derivatized as described below.

2. Oxidation Method

Ten 90 mm pads were reacted with 1 liter of 0.5M sodium metaperiodate at room temperature for 3 hours on a Nalgene plastic filter, the bottom membrane of which had been removed. The pads were washed extensively with water, and then reacted with 2% adipic dihydrazide, (Aldrich Chemical Co., Milwaukee, Wis.) at pH 7.4 for 4 hours. For each 1 liter of hydrazide solution, approximately 10 pads were treated. At the end of 4 hours, solid sodium cyanoborohydride (0.1 mol) was added to the solution and reacted overnight, and finally the pads were extensively washed with water on the Nalgene filter.

ATP 5.5 g (0.01M) was dissolved in 1 liter of deionized water at room temperature, and the pH was adjusted to 4.5 using 10N sodium hydroxide solution. Sodium metaperiodate, 3.2 g (0.015M) was dissolved in 500 mL of water separately in a beaker and the pH was adjusted to 4.5. Care was taken to cover the periodate solution in order to minimize the exposure to light. The contents of the two beakers were mixed well and kept in the dark for 3 hours. The resulting solution of oxidized ATP was added to 12 adipic dihydrazide-treated filter pads and the pads allowed to stand overnight at room temperature. Solid sodium cyanoborohydride 3.14 g (0.05M, Sigma) was then added to 1 liter of the ATP solution and reacted for an additional 4 hours with the pads. Finally the pads were extensively washed with water to remove the excess ATP and sodium cyanoborohydride.

3. Oxidation method—8 hour hydrolysis

Filter pads were hydrolyzed for 8 hours in 1N sodium hydroxide as described for the 44 hour hydrolysis in examples A1 and A2. The pads were then oxidized using sodium metaperiodate and modified with adipic dihydrazide. ATP was immobilized as described above.

B. Preparation of hollow-fibers with ATP covalently attached

Polyethersulfone hollow-fibers (thirty-six bundles, each containing 90 hollow fibers of 1500 microns outside diameter, and 1000 micron inside diameter) prepared as described in copending application 07/956432 on page 87 were placed in a container with slots for the individual bundles, and washed with 20 liters of acetonitrile for 16 hours. The container was provided with ports for draining and a pump for recirculating the liquids to the top of the container, as well as an on-line heater to heat the solutions as needed, and a reservoir for mixing. The acetonitrile was then drained from the container, and the fibers were washed twice for 10 minutes with 20 liters of deionized water. The fibers were then reacted with a solution of 27 liters of deionized water, 3 liters of ethylene glycol diglycidyl ether (EGDGE, Aldrich Chemical Co., Milwaukee, Wis.) and 240 grams of 50% sodium hydroxide solution. The solution was allowed to circulate through the fibers in the container for 3 hours, drained from the container, and the fibers were washed twice for 10 minutes with 20 liters of deionized water. The fibers were reacted with a solution of 27 liters of deionized water, 2 kg of 30% polyethyleneimine solution (PEI) (Epomin P-1000, Aceto Corporation, Lake Success, N.Y.) and 1440 grams of 50% sodium hydroxide solution. The solution was allowed to circulate through the fibers in the container for 5 minutes and the on-line heater was then set such that when the solution was circulated, the temperature of the solution in the container reached 75° C. The solution was circulated for 3 hours, drained from the container, and the fibers washed twice for 10 minutes with 20 liters of deionized water. The water was drained and 30 liters of fresh deionized water was added to the container and allowed to circulate for 16 hours. The water was drained, and replaced with 27 liters of deionized water. Two hundred forty grams of premixed solid phosphate buffer salts (Sigma Chemical Co., St. Louis, Mo.) was added to the reservoir, and allowed to mix for 5 minutes to achieve pH 7.4. Three liters of glutaraldehyde solution (25%, Aldrich Chemical Co.) was added to the reservoir and mixed for 5 minutes. The solutions were circulated through the fibers in the container for 4 hours, drained, and rinsed with deionized water 4 times as described previously. A second PEI coating was applied to the fibers by using a solution made up of 27 liters of deionized water and 2 kg of PEI solution, and mixing for 5 minutes. The contents were allowed to circulate at room temperature for 2 hours, and the contents drained. The fibers were then washed with 20 liters of deionized water 4 times, with the final wash circulating for 16 hours. The water was drained, and replaced with 27 liters of deionized water. Two hundred forty grams of premixed solid phosphate buffer salts (Sigma Chemical Co., St. Louis, Mo.) was added to the reservoir, and allowed to mix for 5 minutes to achieve pH 7.4. Three liters of glutaraldehyde solution (25% Aldrich Chemical Co) was added to the reservoir and mixed for 5 minutes. The solutions were circulated through the fibers in the container for 4 hours, drained and rinsed with deionized water 4 times as described previously.

The water was drained and 30 liters of deionized water was added to the reservoir. Adipic dihydrazide, 600 g(Aceto Corporation), and sodium cyanoborohydride, 100 g (Aldrich Chemical Co.) were added to the reservoir and mixed for 5 minutes. The pH of the solution was adjusted to 7.0 using 5% sodium hydroxide and 1:10 diluted hydrochloric acid solution. The solution was circulated through the fibers for 5 hours at room temperature. The contents were drained, and washed 4 times with deionized water as described previously, and dried at 37° C. for 16 hours. The fibers were stored at room temperature until used.

Ninety hydrazide-treated hollow fibers (40 cm long, 1.5 mm outside diameter and 1 mm inside diameter, approximately 10 g dry weight) were cut into 10 cm lengths, and inserted into a 1 liter Nalgene plastic flask. One liter of oxidized ATP at pH 4.5 was then introduced into the flask and mixed overnight. The pH of the oxidized ATP solution was adjusted to 7.4, and solid sodium cyanoborohydride, 3.14 g (0.05M) was then added to the flask, and mixed for an additional 4 hrs. The solution was drained from the fibers, and the fibers were extensively washed with water and dried in air.

C. Preparation of aminated chromatography beads with ATP covalently attached Aminated Hyper D™ beads (available from Sepracor, Inc., Marlboro, Mass.) M grade (average size 85 µm, 36 µm eq/mL amino groups), 100 g was placed in a 1 L Nalgene plastic flask. Hyper D™ beads are porous silica beads having a gel composed of crosslinked aminated methacrylamide derivative in the pores, as described in U.S. application Ser. No. 07/956,404 filed Oct. 5, 1992. One liter of oxidized ATP 5.5 g (0.01M) prepared as described above was added to the flask, and mixed in a rotating mixer for 3 hours. At the end of 3 hours, the pH of the supernatant was adjusted to 7.4 using 10N sodium hydroxide, and mixed overnight. Solid sodium cyanoborohydride, 3.14 g (0.05M) was added to the flask, and mixed for an additional 4 hrs. The beads were transferred to a one liter sintered glass funnel (25–50 µm frit), washed extensively with water, and dried in air. Two other grades of aminated Hyper D beads were similarly derivatized with ATP. The three grades are designated $C^a$, $C^b$ and $C^c$ in the tables below.

D. Preparation of 2,3-Diphospho-D-glycerate (DPG) Filter Pads

The polypropylene/cellulose acetate filter pads were hydrolyzed with 1N NaOH for 44 hours and oxidized with sodium meta-periodate as described previously. A 1M solution of ethylenediamine (Aldrich Chemicals), pH 7.5, 1.5 liters, was made by adjusting the pH with concentrated HCl, and reacted with the oxidized pads (13) for 16 hours as described for adipic dihydrazide. Solid sodium cyanoborohydride (Sigma) was added to the ethylenediamine solution to bring the concentration to 0.1M in sodium cyanoborohydride, and reacted for an additional 4 hours. The filters were washed extensively with deionized water to remove excess cyanoborohydride and ethylenediamine, and dried overnight at 30° C.

2,3-Diphospho-D-glyceric acid, pentasodium salt, (DPG), 200 mg (Sigma) was dissolved in 50 ml of 0.1M MES buffer prepared by dissolving 1.92 g of 2-(N-morpholino)ethane sulfonic acid (Sigma Chemicals) in 100 mL deionized water and adjusting the pH to 4.5 with 1N sodium hydroxide solution. 1-Ethyl-3-(3-dimethylaminopropyl) carbodiimide (EDAC), 200 mg, (Sigma) was dissolved in 10 mL of 0.1M MES buffer and the pH adjusted to 4.5 with 1N sodium hydroxide. EDAC solution, 2.5 mL, was mixed with 50 mL of DPG solution for 1 minute, and gently poured onto two dry 90 mm filter pads that had been modified with ethylenediamine. The pads were supported in a 1 L Nalgene plastic filter holder without the bottom membrane. After 15 minutes the DPG solution was removed from the filter pads by suction, and another 2.5 mL of EDAC solution was added gently to the filter pads on the filter. This procedure was repeated two more times until all the EDAC solution was added. The DPG/EDAC solutions were allowed to drain through the filter pads under gravity, and every 30 minutes the pads were dried by suction. The filtrate was gently poured on top of the pads and the process repeated for 7 more times. The filter pads were washed with 2 liters of 1M sodium chloride, and then extensively washed with deionized water to remove unreacted DPG and EDAC. The filters were dried in air at 30° C., and stored at 30° C. until used for human hemoglobin testing.

TESTING OF ATP MODIFIED MATRICES

E. Testing Using Bovine Hemoglobin Solutions

Bovine hemoglobin solution, 0.5 mg/mL in 0.9% NaCl, was made by dissolving 125 mg of bovine hemoglobin (BHG) (Sigma Chemicals, H-2625) in 250 mL of 0.9% NaCl for 1 hour at room temperature, and filtered through a 0.22 μm cellulose acetate membrane filter. Measured volumes of control or ATP-derivatized pads, beads, or membranes were placed in 15 mL polypropylene centrifuge tubes, and calculated amounts of hemoglobin solution were added and mixed for 1 hour. The tubes were centrifuged and the absorbance at 405 nm was measured for each sample supernatant and the original hemoglobin solution. The amount of hemoglobin uptake was measured from depletion and expressed as uptake per unit matrix volume. Table I gives the values for the non-specific adsorption of BHG to control pads and of specific binding of BHG to ATP-immobilized pads prepared according to Example A2.

TABLE I

| Material from | Quantity (mL) | mL BHG solution | mg BHG offered | mg BHG in Supernatant | % BHg Removed | BHG Cap. mg/mL |
|---|---|---|---|---|---|---|
| Example A2 | 3 | 9 | 4.5 | 0.012 | 99.7 | >1.49 |
| Unmodified filter pads | 3 | 9 | 4.5 | 3.83 | 14.8 | 0.22 |

In a separate set of experiments, shown in Table II, the specific binding of BHG was examined with ATP immobilized filter pads, hollow-fibers and three grades of chromatography beads as well as a commercially available ATP bound to agarose gel, (Sigma Chemical Co., St. Louis, Mo.) which was included for comparison. The results show that of the test devices, ATP modified pads gave the highest capacity for BHG at 1.4 mg/mL, followed by hydrazidetreated hollow fibers at 1.38 mg/mL and the beads at 1.28 mg/mL. It should be noted the BHG results are a qualitative indicator of human hemoglobin (HHG) capacity, as there are compositional and structural differences between bovine and human hemoglobins.

TABLE II

| Material from | Quantity (mL) | mL BHG solution | mg BHG offered | mg BHG in Supernatant | BHG Cap. mg/mL |
|---|---|---|---|---|---|
| Example A(2) | 3 | 9 | 4.5 | 0.31 | 1.4 |
| Example B | 1 | 6 | 3 | 1.62 | 1.38 |
| Example C$^a$ | 1 | 6 | 3 | 1.72 | 1.28 |
| Example C$^b$ | 1 | 6 | 3 | 1.94 | 1.06 |
| Example C$^c$ | 1 | 6 | 3 | 1.03 | 0.97 |
| Agarose ATP (Sigma) | 1 | 6 | 3 | 1.23 | 1.77 |

F. Testing Using Human Hemoglobin (HHG) Solutions

To the ATP, DPG or control immobilized matrices in 15 mL centrifuge tubes, calculated volumes of human hemoglobin solutions were added and mixed for 1 hour. The amount of hemoglobin uptake was measured from depletion and expressed in uptake per unit matrix volume. As controls, filter pads that had not been exposed to alkaline hydrolysis were tested (1) as purchased and (2) after treatment with sodium metaperiodate, followed by adipic dihydrazide and ATP as described in A. The hemoglobin solutions contained 150 mg % HHG. The results are shown in Table III. Neither of the controls exhibited useful hemoglobin uptake.

TABLE III

| Material from example | Amount of test material (mL) | amount of HHG solution (mL) | mg % in Supernatant | HHG capacity (mg/mL) |
|---|---|---|---|---|
| Unmodified + ATP | 3 | 6 | 143 | 0.132 |
| Unmodified | 3 | 6 | 140 | 0.192 |
| Example A(2) | 3 | 3 | 4 | 2.912 |

Another set of experiments was carried out using 800 mg % of free HHG for ATP (examples A-C) and 793 mg % for DPG (example D). Table IV gives the binding of HHG to the pads, the hollow-fibers, and the beads. The results show that the pads with ATP bound 9.5 HHG/mL of pads, the hydrazide membranes bound 3.1 mg HHG/mL of membrane, and the best Hyper D™ beads bound 2.1 mg HHG/mL of settled beads. The control ATP on agarose bound around 11.6 mg HHG/mL. The pads with DPG bound 1.7 mg/mL of HHG.

TABLE IV

| Material from example | Amount of test material (mL) | amount of HHG solution (mL) | mg % in Supernatant | HHG capacity (mg/mL) |
|---|---|---|---|---|
| A(2) | 3 | 6 | 327 | 9.46 |
| B | 2 | 6 | 698 | 3.06 |
| C$^a$ | 5 | 5 | 589 | 2.11 |
| C$^b$ | 5 | 5 | 752 | 0.48 |
| C$^c$ | 5 | 5 | 706 | 0.91 |
| D | 3 | 6 | 708 | 1.7 |
| agarose ATP | 1.5 | 3 | 218 | 11.64 |

One dry 90 mm (12 mL) pad from Example A(3) was placed in a Petri dish, and 25 mL of a HHG solution containing 185 mg % HHG added to the Petri dish. The solution was swirled and allowed to mix with the pad for 1 hour. The concentration of HHG in the supernatant solution was measured and was found to be 185 mg %. This is interpreted to indicate that eight hours or less at 23° C. room temperature in 1N NaOH will not provide adequate hydrolysis for effective functionalization.

G. Testing Using Packed Human Red Blood Cells

Small (<5 mL) samples were tested similar to the ones described for hemoglobin solution, by adding packed human red blood cells (containing hemoglobin) mixing for 1 hour, and measuring the hemoglobin left in the supernatant. The amount of hemoglobin uptake was measured from depletion and expressed in uptake/unit matrix volume. The experiments were carried out using packed red blood cells containing 622 mg % free HHG and 36% hematocrit. Table V gives the results of capacity measurements of the matrices in the presence of packed red blood cells. The results show that under the conditions tested, tumbling in a test tube for 1 hr, extensive lysis occurs and more HHG is produced in the supernatant than was originally present in the control test packed red cell solution. The only exception is in the case of filter pads, which gave a capacity of 2.2 mg HHG/mL, despite some break up of the cells.

TABLE V

| Material from example | Amount of test material (mL) | amount of red blood cells (mL) | mg % of HHG in supernatant | HHG capacity (mg/mL) |
|---|---|---|---|---|
| A(2) | 3 | 8 | 698 | 2.17 |
| B | 2 | 8 | 1483 | NA* |
| C$^a$ | 5 | 7 | 6781 | NA* |
| C$^b$ | 5 | 7 | 10250 | NA* |
| C$^c$ | 5 | 7 | 10250 | NA* |
| agarose ATP | 1.5 | 4.2 | 425 | 8.4 |

*NA = not available; cannot be calculated because of hemolysis

H. Testing Using Pads in Device

The ATP modified filter pads were tested in a filter pad holding device. Experiments were carried out using filter pads, beads and membranes with packed red blood cells. The beads (29 mL) or hollow-fiber membranes (20 mL) were not tested alone, but were sandwiched between two 90 mm ATP-modified pads (12 mL). Two hundred mL of packed red blood cells (20% hematocrit in the case of beads, and 36% hematocrit in the case of hollow-fiber membranes) were passed through the device in 10 minutes. The amount of hemoglobin uptake was measured from depletion and expressed as uptake/unit matrix volume.

Results of filter pad devices with Hyper D beads between the pads are given in Table VI. The results show that the supernatant HHG concentration has increased from the starting 622 mg % to 829 mg % after filtration. Clearly, as in the case of the test tube measurements, the beads appear to have lysed the red cells and liberated HHG. These results show that the use of beads is not viable. Results of filter pad devices with hydrazide membrane-ATP between the pads are also given in Table VI. The results show that the supernatant HHG concentration has decreased from the starting 622 mg % to 393 mg % after filtration. The total free HHG presented was 796 mg and after filtration 503 mg was present in the filtrate, corresponding to the removal of 293 mg. This corresponds to a 37% removal of free HHG.

TABLE VI

| Material | mL blood cells | mg % in supernatant | HHG capacity (mg/mL) |
|---|---|---|---|
| Pads plus beads | 200 | 829 | NA* |
| Pads plus hollow-fibers | 200 | 393 | 6.67 |

*NA = not available; cannot be calculated because of hemolysis

The HHG removal capacity for the device with ATP immobilized pads and the membranes may be calculated from the data obtained from HHG solution experiments. The maximum HHG capacities for the ATP pads and ATP membranes were found to be 9.46 and 3.06 mg HHG/mL respectively. Based on these data, the expected capacities for the pads and membranes may be calculated as given below.

| ATP Pads and Membrane Device | | | |
|---|---|---|---|
| Chemistry/ Matrix | Dimension | Matrix Volume | Expected HHG Capacity |
| ATP/Pads | 90 mm × 1.9 mm | 12 mL | 113.5 mg |
| ATP/Membranes | 5 g, cut pieces | 20 mL | 61.2 mg |
| ATP/Pads | 90 mm × 1.9 mm | 12 mL | 113.5 mg |
| For total device expected | | 44 mL | 288.2 mg |
| Measured HHG capture capacity on device | | | 293.2 mg |

The results show that the estimation of HHG capacity using HHG in solution may be used to estimate the expected capacity in the device.

While the invention has been particularly shown and described with reference to preferred embodiments thereof, it will be understood by those skilled in the art that other changes in form and details may be made therein without departing from the spirit and scope of the invention.

We claim:

1. A filter for removing hemoglobin from whole blood or a blood fraction, comprising a shape-sustaining laid textile web having a thickness of 1 to 8 mm and a bulk density of 0.05 to 0.4 g/cm$^3$, said web comprising:

(a) a plurality of interlocked textile fibers with average deniers between 0.05 and 0.75 and average lengths between 3 mm and 15 mm, said textile fibers being substantially uniformly distributed in said web so as to form a matrix of the textile fibers with spaces between adjacent interstices of interlocked fibers; and (b) a plurality of fibrillated particles of surface-modified polymeric material having a surface area of 5 to 60 square meters per gram substantially disposed within said spaces of the matrix, said fibrillated particles having a plurality of fine fibrils which are interlocked with adjacent textile fibers of said spaces such that the fibrillated particles are not substantially displaceable from said web during filtration of said blood;

wherein the weight ratio of the fibrillated particles to the textile fibers is between 1:99 and 40:60; and wherein said surface-modified polymeric material is cellulose acetate covalently linked to a ligand for hemoglobin; and wherein said textile fibers are hemolytically inert and stable to alkaline hydrolysis.

2. A filter according to claim 1 wherein said ligand for hemoglobin is selected from the group consisting of inositol hexaphosphate, adenosine triphosphate (ATP), pyridoxal phosphate, 2,3-diphosphoglycerate (DPG), adenosine diphosphate (ADP), and adenosine phosphate.

3. A filter according to claim 2 wherein said ligand is ATP or DPG.

4. A filter according to claim 1 wherein said ligand is attached to said cellulose acetate via a dihydrazide or diamine linker.

5. A filter according to claim 4 wherein said linker is adipic dihydrazide.

6. A filter according to claim 1 wherein said textile fibers are one or more of polyolefin, polyamide, polysulfone, polyester, polyvinyl alcohol, and poly(ethylene-vinyl alcohol) copolymer fibers.

7. A filter according to claim 6 wherein said textile fibers are polyolefin fibers.

8. A method for removing hemoglobin from whole blood or a blood fraction comprising passing said blood through a filter according to claim 3.

* * * * *

UNITED STATES PATENT AND TRADEMARK OFFICE
CERTIFICATE OF CORRECTION

PATENT NO.   : 5,456,835
DATED        : October 10, 1995
INVENTOR(S)  : Castino et al.

It is certified that error appears in the above-indentified patent and that said Letters Patent is hereby corrected as shown below:

In the claims:

Column 16, line 17, delete "3" and insert therefor, --1--.

Signed and Sealed this

Thirteenth Day of February, 1996

Attest:

BRUCE LEHMAN

*Attesting Officer*  *Commissioner of Patents and Trademarks*